US011826256B2

(12) United States Patent
Conrad

(10) Patent No.: US 11,826,256 B2
(45) Date of Patent: Nov. 28, 2023

(54) FORMING A PILOT HOLE

(71) Applicant: Zimmer, Inc., Warsaw, IN (US)

(72) Inventor: Steven Conrad, Albion, IN (US)

(73) Assignee: Zimmer, Inc., Warsaw, IN (US)

( * ) Notice: Subject to any disclaimer, the term of this patent is extended or adjusted under 35 U.S.C. 154(b) by 233 days.

(21) Appl. No.: 17/464,857

(22) Filed: Sep. 2, 2021

(65) Prior Publication Data

US 2022/0061997 A1 Mar. 3, 2022

Related U.S. Application Data

(60) Provisional application No. 63/074,263, filed on Sep. 3, 2020.

(51) Int. Cl.
| | | |
|---|---|---|
| *A61F 2/34* | (2006.01) | |
| *A61B 17/16* | (2006.01) | |
| *A61B 17/92* | (2006.01) | |
| *A61F 2/46* | (2006.01) | |
| *A61F 2/36* | (2006.01) | |
| *A61F 2/30* | (2006.01) | |

(52) U.S. Cl.
CPC ........ *A61F 2/3609* (2013.01); *A61B 17/1604* (2013.01); *A61B 17/1666* (2013.01); *A61B 17/92* (2013.01); *A61F 2/3094* (2013.01); *A61F 2/34* (2013.01); *A61F 2/4609* (2013.01); *A61F 2002/30301* (2013.01); *A61F 2002/30649* (2013.01); *A61F 2002/30985* (2013.01); *A61F 2002/3613* (2013.01); *A61F 2002/3615* (2013.01)

(58) Field of Classification Search
CPC . A61B 17/1604; A61B 17/1666; A61B 17/92; A61B 17/8872; A61B 17/88; A61B 17/1746; A61F 2/4609; A61F 2002/4625; A61F 2002/4627; A61F 2002/4619; B26F 1/14; B26F 1/32
See application file for complete search history.

(56) References Cited

U.S. PATENT DOCUMENTS

| | | | | |
|---|---|---|---|---|
| 4,712,951 | A * | 12/1987 | Brown | ............... B23B 51/0018 606/81 |
| 8,409,230 | B2 * | 4/2013 | Pamichev | .......... A61B 17/1604 606/187 |
| 10,188,407 | B2 * | 1/2019 | Termanini | .......... A61B 17/1746 |

(Continued)

*Primary Examiner* — Tracy L Kamikawa
(74) *Attorney, Agent, or Firm* — SCHWEGMAN LUNDBERG & WOESSNER, P.A.

(57) ABSTRACT

A system can form a pilot hole to secure a securable element, such as an acetabular cup. A saddle can removably attach to the securable element. The saddle can confine a translator and allow the translator to move along a translator axis between a first translator position and a second translator position. A punch element can be movably coupled to the saddle and the translator such that when the saddle is removably attached to the securable element, moving the translator from the first translator position toward the second translator position can advance a tip of the punch element from the saddle through the securable element along a punch axis that is angled with respect to the translator axis. An impaction stem can be coupled to the translator by a joint, such as a ball-and-socket joint, and can impart motion to the translator.

16 Claims, 12 Drawing Sheets

(56) References Cited

U.S. PATENT DOCUMENTS

2009/0234453 A1* 9/2009 Steinberg ........... A61B 17/1617
606/1
2017/0027715 A1* 2/2017 Huang ............... A61B 17/8894
2018/0200068 A1* 7/2018 Goldberg ........... A61B 17/1684

* cited by examiner

FORMING A PILOT HOLE

CLAIM OF PRIORITY

This application claims the benefit of U.S. Provisional Patent Application Ser. No. 63/074,263, filed on Sep. 3, 2020, the benefit of priority of which is claimed hereby, and which is incorporated by reference herein in its entirety.

FIELD OF THE DISCLOSURE

The present disclosure relates generally to a system, such as a screw punch, that can form a pilot hole, and a method for producing a system that can form a pilot hole.

BACKGROUND OF THE DISCLOSURE

In some hip replacement surgeries, an acetabular cup can be mounted against a prepared portion of a patient's pelvis. A convex exterior of the acetabular cup can contact the pelvis bone. A concave interior of the acetabular cup can face a femoral head of a hip implant. When the hip implant is implanted, the femoral head can rotate within the acetabular cup to perform the motion of the hip joint. In some examples, a polyethylene liner can be positioned between a convex exterior of the femoral head and the concave interior of the acetabular cup to prevent contact between the hard surface of the femoral head and the hard surface of the acetabular cup. In some examples, one or more bone screws can fasten the acetabular cup to the pelvis bone.

SUMMARY

In an example, a system for forming a pilot hole to secure a securable element can include: a saddle configured to removably attach to the securable element; a translator confined by the saddle, the saddle allowing the translator to move along a translator axis between a first translator position and a second translator position; a punch element movably coupled to the saddle and the translator such that when the saddle is removably attached to the securable element, moving the translator from the first translator position toward the second translator position advances a tip of the punch element from the saddle through the securable element along a punch axis that is angled with respect to the translator axis; and an impaction stem coupled to the translator by a joint and configured to impart motion to the translator.

In another example, a method for producing a system for forming a pilot hole to secure a securable element can include, with a three-dimensional printer: printing a saddle configured to removably attach to the securable element; printing a translator confined by the saddle, the saddle allowing the translator to move along a translator axis between a first translator position and a second translator position; printing a punch element movably coupled to the saddle and the translator such that when the saddle is removably attached to the securable element, moving the translator from the first translator position toward the second translator position advances a tip of the punch element from the saddle through the securable element along a punch axis that is angled with respect to the translator axis; and printing an impaction stem coupled to the translator by a joint and configured to impart motion to the translator.

In still another example, a system for forming a pilot hole can include: an acetabular cup; a saddle configured to removably attach to the acetabular cup; a translator confined by the saddle, the saddle allowing the translator to move along a translator axis between a first translator position and a second translator position; a punch element movably coupled to the saddle and the translator such that when the saddle is removably attached to the acetabular cup, advancing the translator toward the acetabular cup to move the translator from the first translator position toward the second translator position advances a tip of the punch element from the saddle through an aperture in the acetabular cup into the bone along a punch axis that is angled with respect to the translator axis; and an impaction stem coupled to an end of the translator by a ball-and-socket joint and configured to impart motion to the translator.

BRIEF DESCRIPTION OF THE DRAWINGS

Corresponding reference characters indicate corresponding parts throughout the several views. Elements in the drawings are not necessarily drawn to scale. The configurations shown in the drawings are merely examples and should not be construed as limiting in any manner.

DETAILED DESCRIPTION

Figure 1:
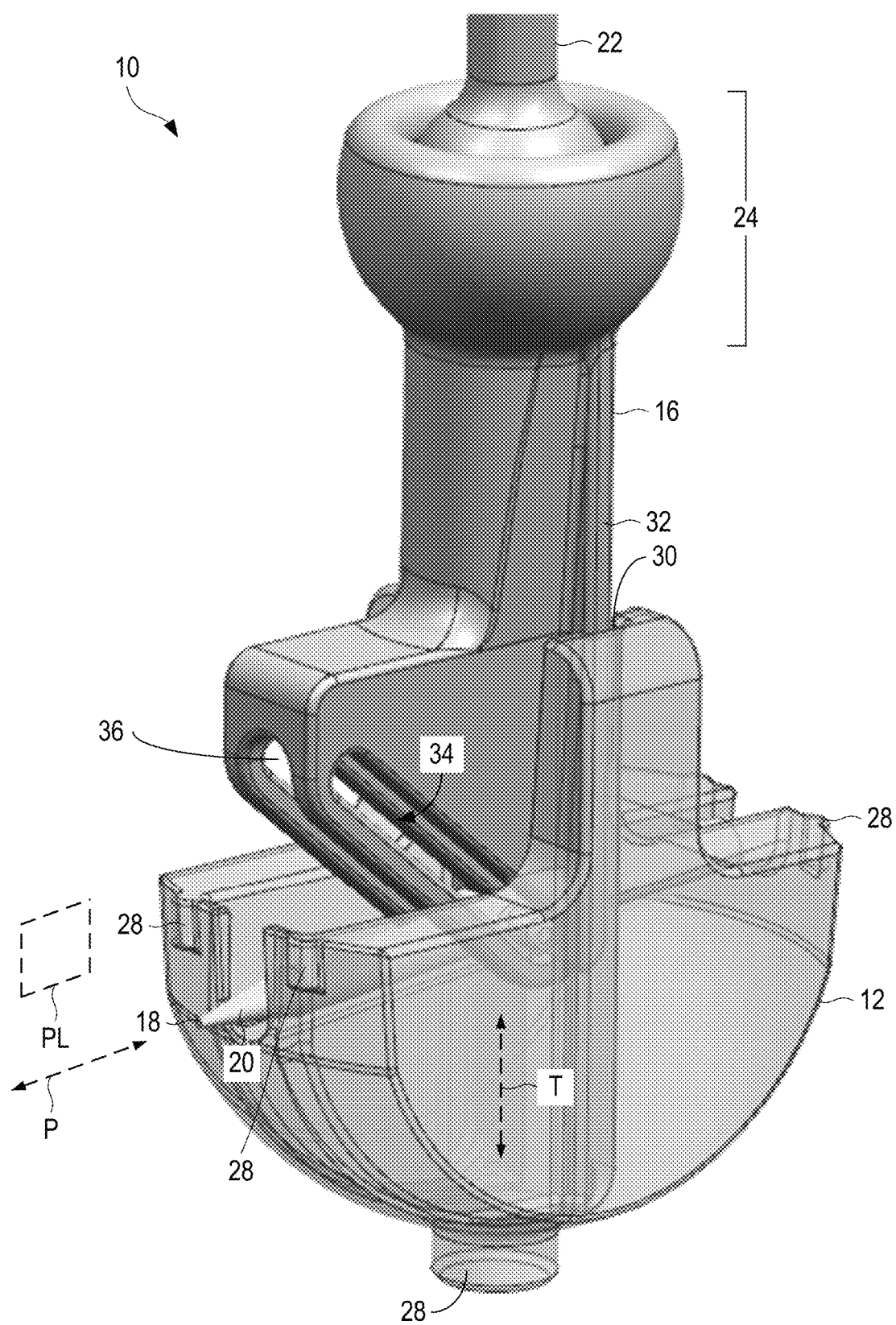
FIG. 1 shows a perspective view of an example of a system, in which a translator is positioned at the first translator position, in accordance with some examples.

A system, such as a punch, can simplify the forming of a pilot hole to secure a securable element, such as an acetabular cup. For example, the system can removably attach to an acetabular cup. While attached, the system can redirect an applied force to form the pilot hole through a specified aperture, of a plurality of apertures, through the acetabular cup, optionally in a direction that is orthogonal or generally orthogonal to a surface of the acetabular cup. The pilot hole can be formed to later accommodate a bone screw that can attach the acetabular cup to a prepared portion of a patient's pelvis.

The system can form the pilot hole with a specified location and with a specified orientation, such as through a selected aperture of a plurality of apertures that extend through the acetabular cup. As a result, the mechanical features of the system can allow a practitioner to grip the system and manipulate the system in a manner that is convenient for the practitioner, without requiring the practitioner to manipulate a hole-creating element at a specified location and/or in a specified direction. Consequently, using the system to form the pilot hole can be more convenient and more precise than drilling the pilot hole by hand, especially for configurations in which the specified hole in the acetabular cup is difficult to access.

FIGS. 1-11, described in detail below, show various elements of an example of a system that can form a pilot hole, in accordance with some examples. These figures use a common numbering scheme for the system elements.

The system 10 can include a saddle 12 that can removably attach to the securable element 14. The saddle 12 can confine a translator 16 to move along a translator axis (T) between a first translator position (for example, in FIGS. 1, 5, and 9) and a second translator position (for example, in FIGS. 2, 6, 7, and 11). The translator 16, when moved from the first translator position toward the second translator position, can advance a tip 18 of a punch element 20 from the saddle 12 through the securable element 14 along a punch axis (P) that is angled with respect to the translator axis (T). An impaction stem 22, coupled to the translator 16 by a joint 24, such as a ball-and-socket joint, can impart motion to the translator 16.

To form the pilot hole, a practitioner can grip the impaction stem 22 and force the impaction stem 22 toward (or away from) the saddle 12. The joint 24 can allow the practitioner to hold the impaction stem 22 at any suitable orientation, which need not align with an axis of the pilot hole. The joint 24 can further allow the practitioner to vary the orientation of the impaction stem 22 over the stroke of the hole-forming motion (e.g., as the practitioner causes the translator 16 to move between the first translator position and the second translator position). Compared with the case of manipulating a drill to drill the pilot hole by hand, using the system 10 described herein can improve flexibility for the practitioner, such as by allowing the practitioner to hold an element at any suitable orientation while forming the pilot hole, and allowing the practitioner to vary the orientation of a held element, while forming the pilot hole.

FIG. 1 shows a perspective view of an example of a system 10, in which the translator 16 is positioned at the first translator position, in accordance with some examples.

Figure 2:
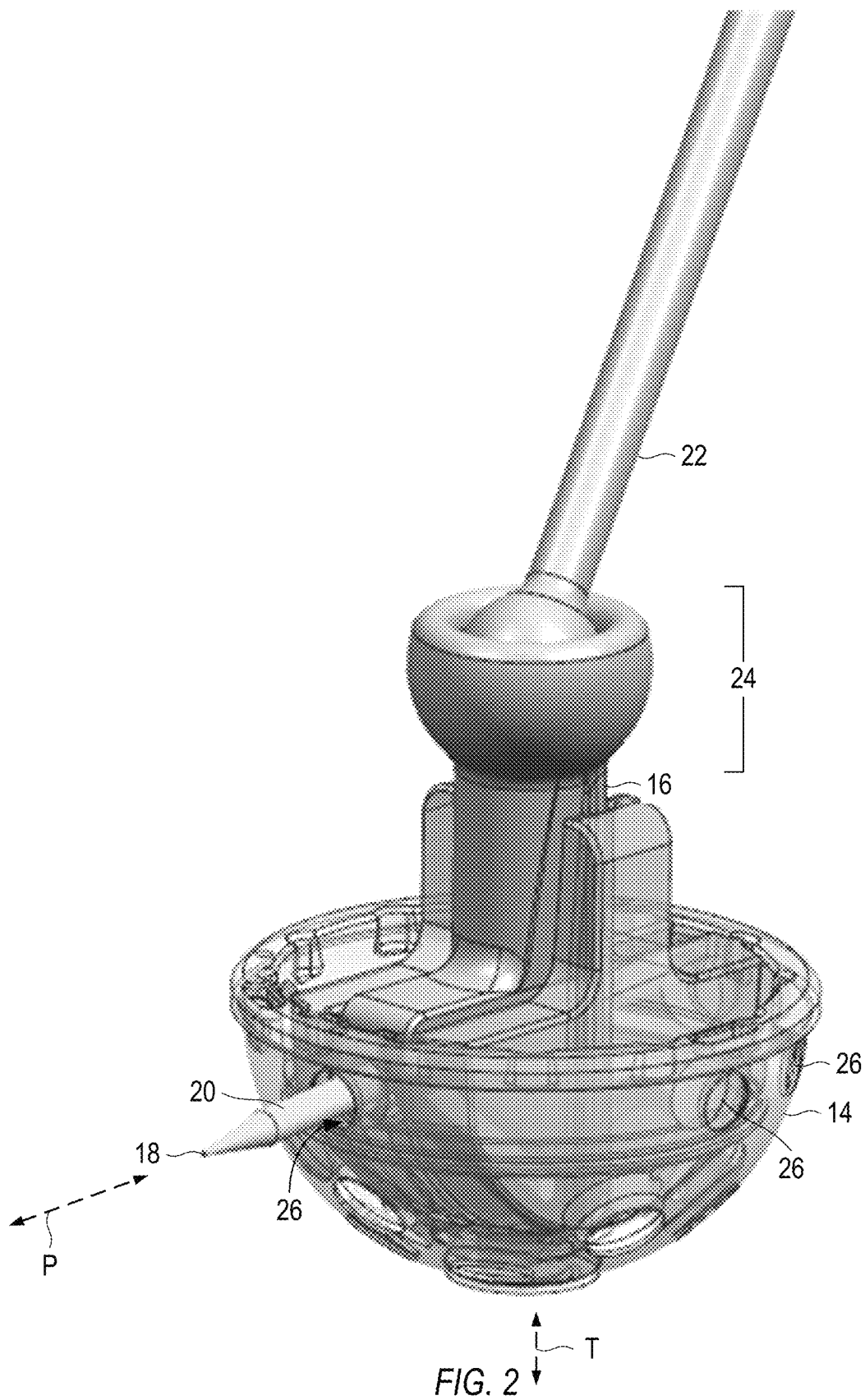
FIG. 2 shows a perspective view of an example of the system of FIG. 1 and a securable element, in which the translator is positioned at the second translator position, in accordance with some examples.

FIG. 2 shows a perspective view of an example of the system 10 and a securable element 14, in which the translator 16 is positioned at the second translator position, in accordance with some examples.

Figure 3:
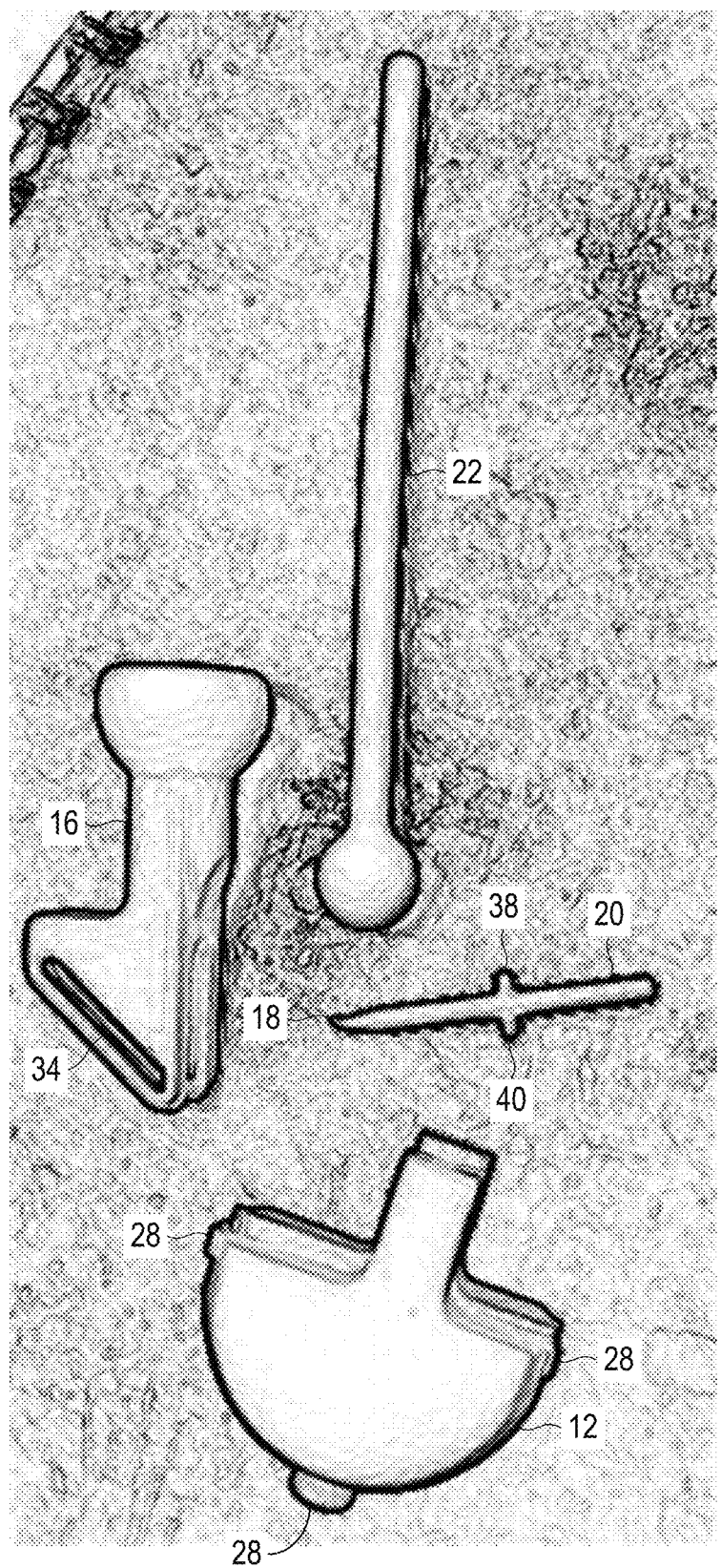
FIG. 3 shows a disassembled view of individual elements of the system of FIG. 1, in accordance with some examples.

FIG. 3 shows a disassembled view of individual elements of the system 10, in accordance with some examples.

Figure 4:
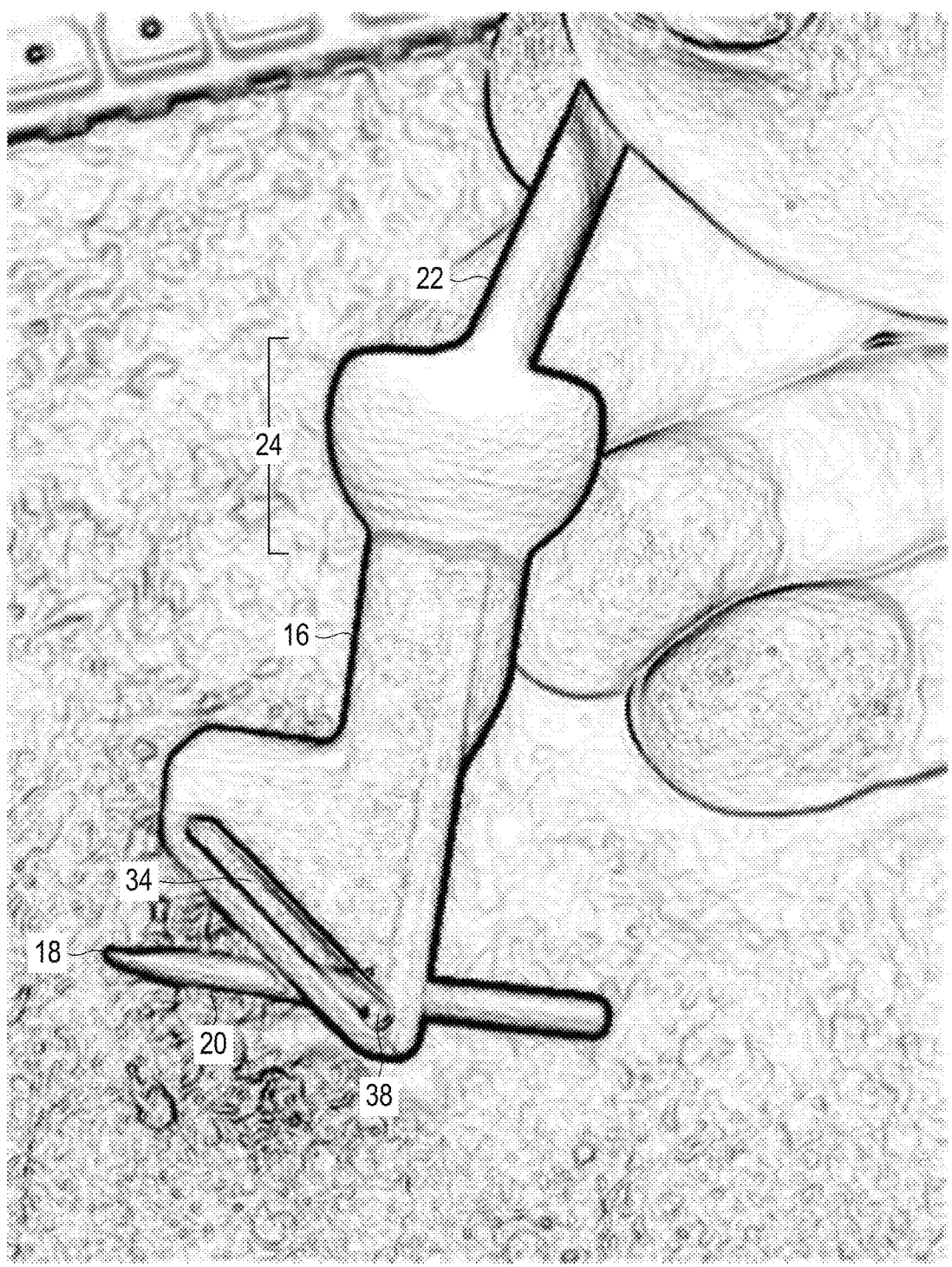
FIG. 4 shows a partially-assembled view of the translator, the punch element, and the impaction stem of the system of FIG. 1, in accordance with some examples.

FIG. 4 shows a partially-assembled view of the translator 16, the punch element 20, and the impaction stem 22 of the system 10, in accordance with some examples.

Figure 5:
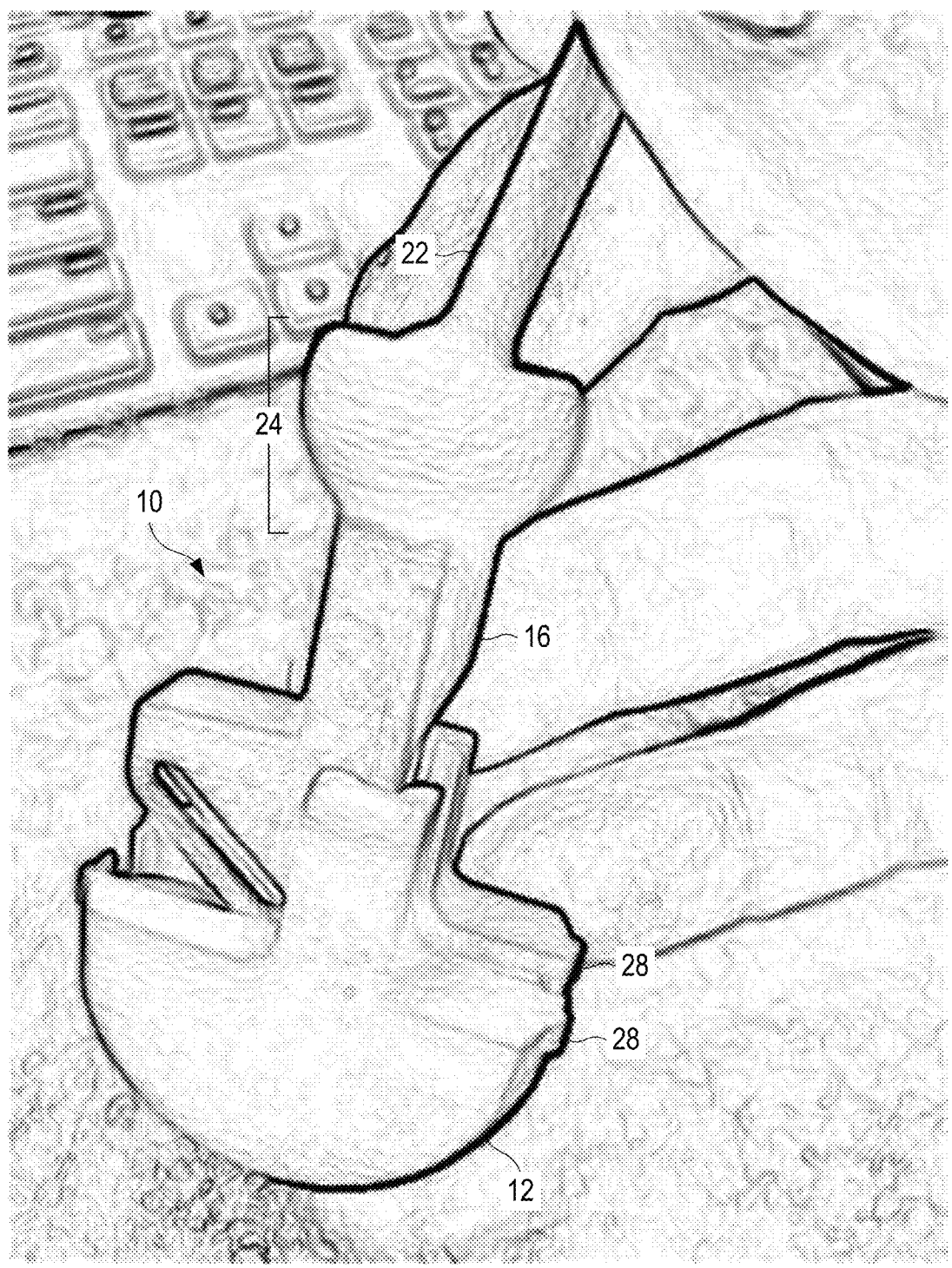
FIG. 5 shows a perspective view of the system of FIG. 1, in which the translator is positioned at the first translator position, in accordance with some examples.

FIG. 5 shows a perspective view of the system 10, in which the translator 16 is positioned at the first translator position, in accordance with some examples.

Figure 6:
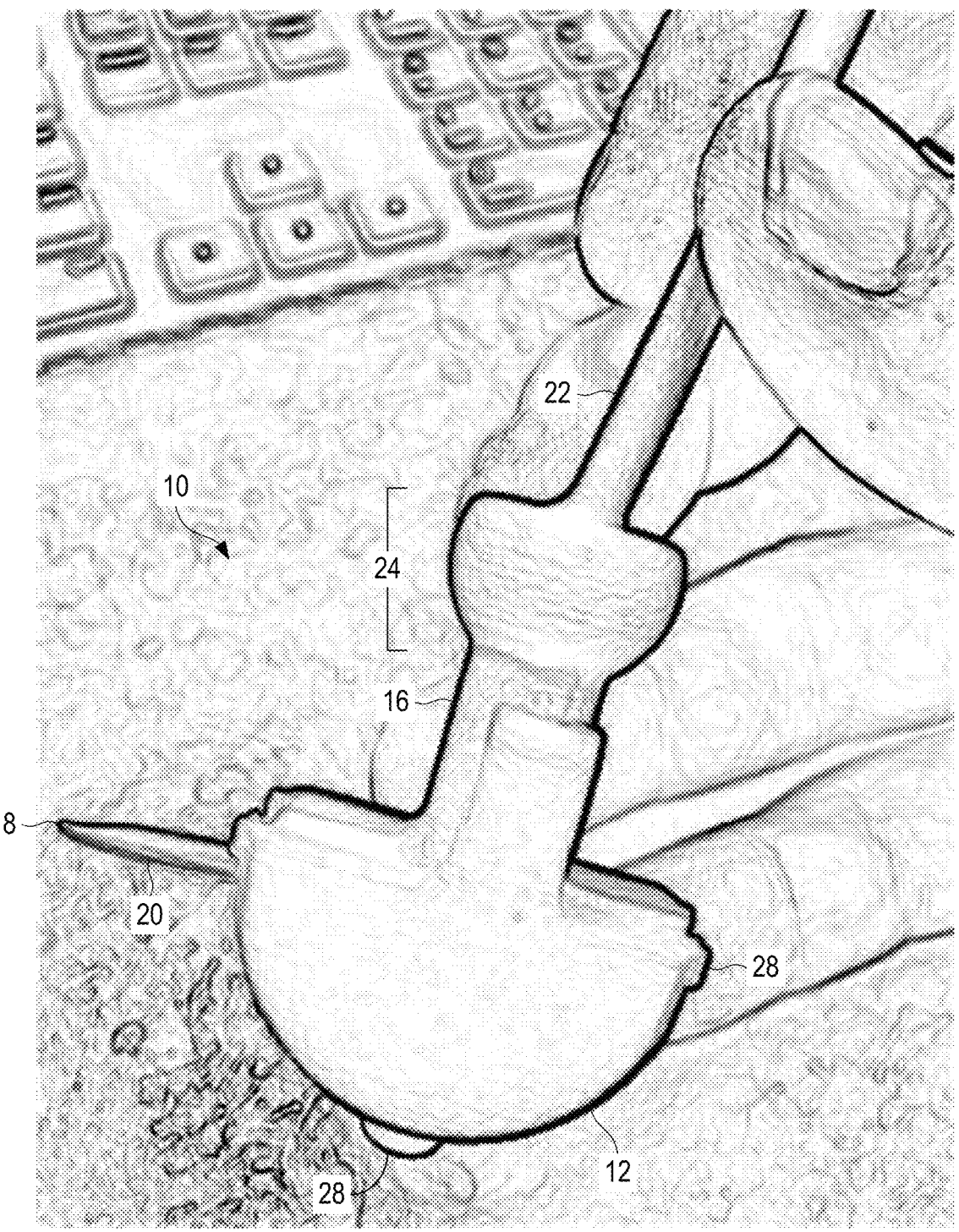
FIG. 6 shows a perspective view of the system of FIG. 1, in which the translator is positioned at the second translator position, in accordance with some examples.

FIG. 6 shows a perspective view of the system 10, in which the translator 16 is positioned at the second translator position, in accordance with some examples.

Figure 7:
FIG. 7 shows a perspective view of the system of FIG. 1 and a securable element, in which the translator is positioned at the second translator position, in accordance with some examples.

FIG. 7 shows a perspective view of the system 10 and a securable element 14, in which the translator 16 is positioned at the second translator position, in accordance with some examples.

Figure 8:
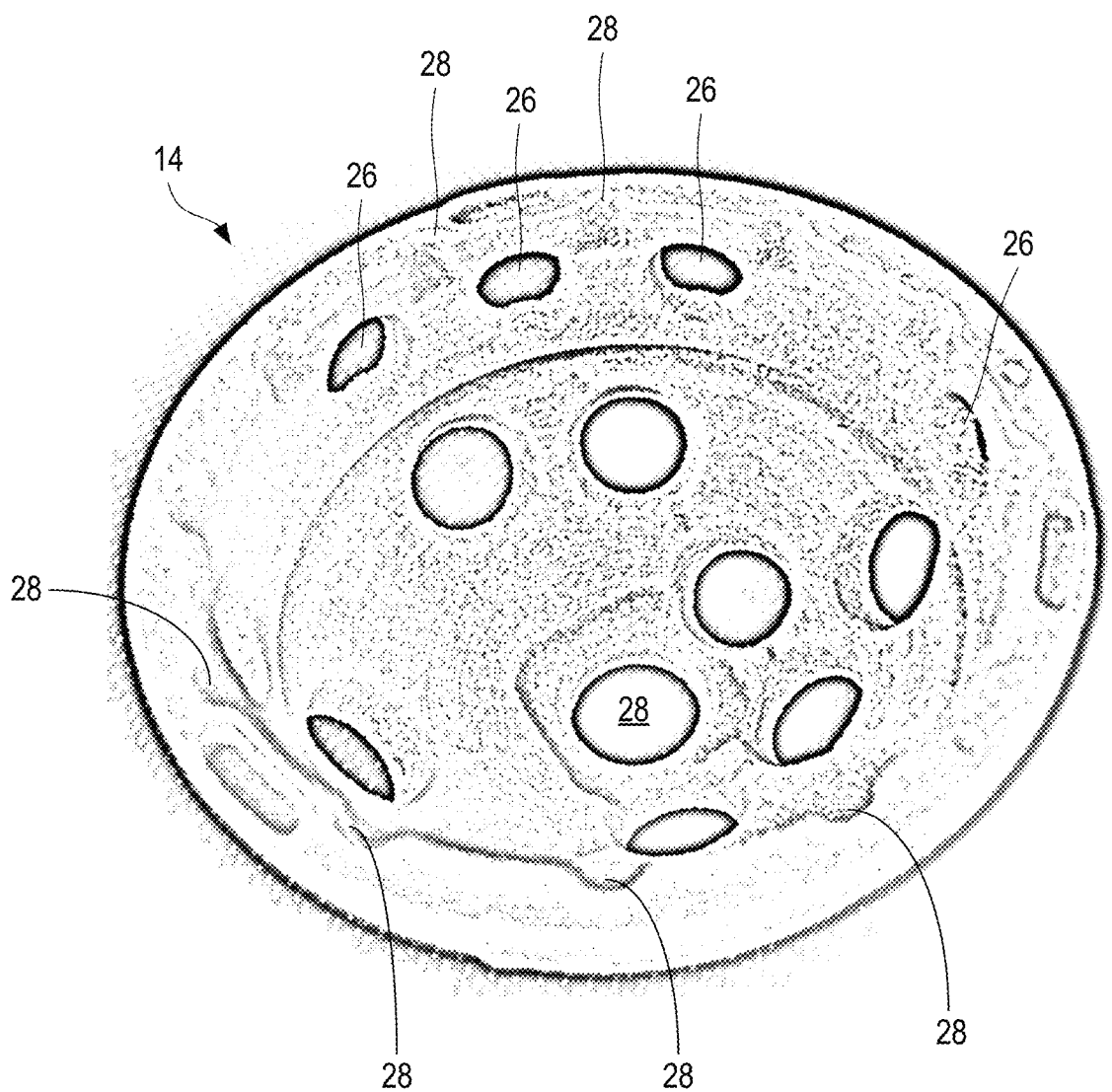
FIG. 8 shows a perspective view of a securable element, in accordance with some examples.

FIG. 8 shows a perspective view of a securable element 14, in accordance with some examples.

Figure 9:
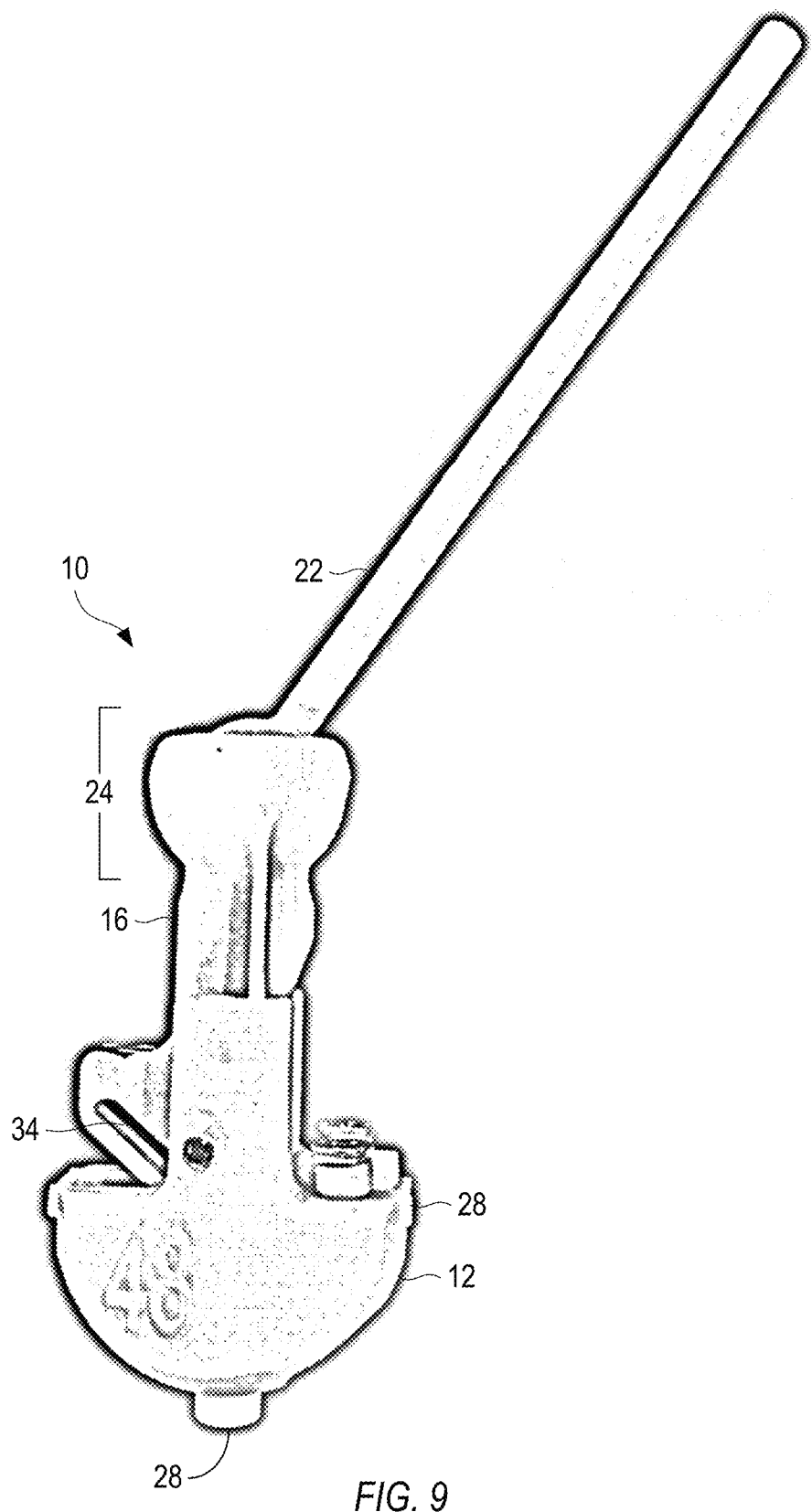
FIG. 9 shows a side view of the system of FIG. 1, in which the translator is positioned at the first translator position, in accordance with some examples.

FIG. 9 shows a side view of the system 10, in which the translator 16 is positioned at the first translator position, in accordance with some examples.

Figure 10:
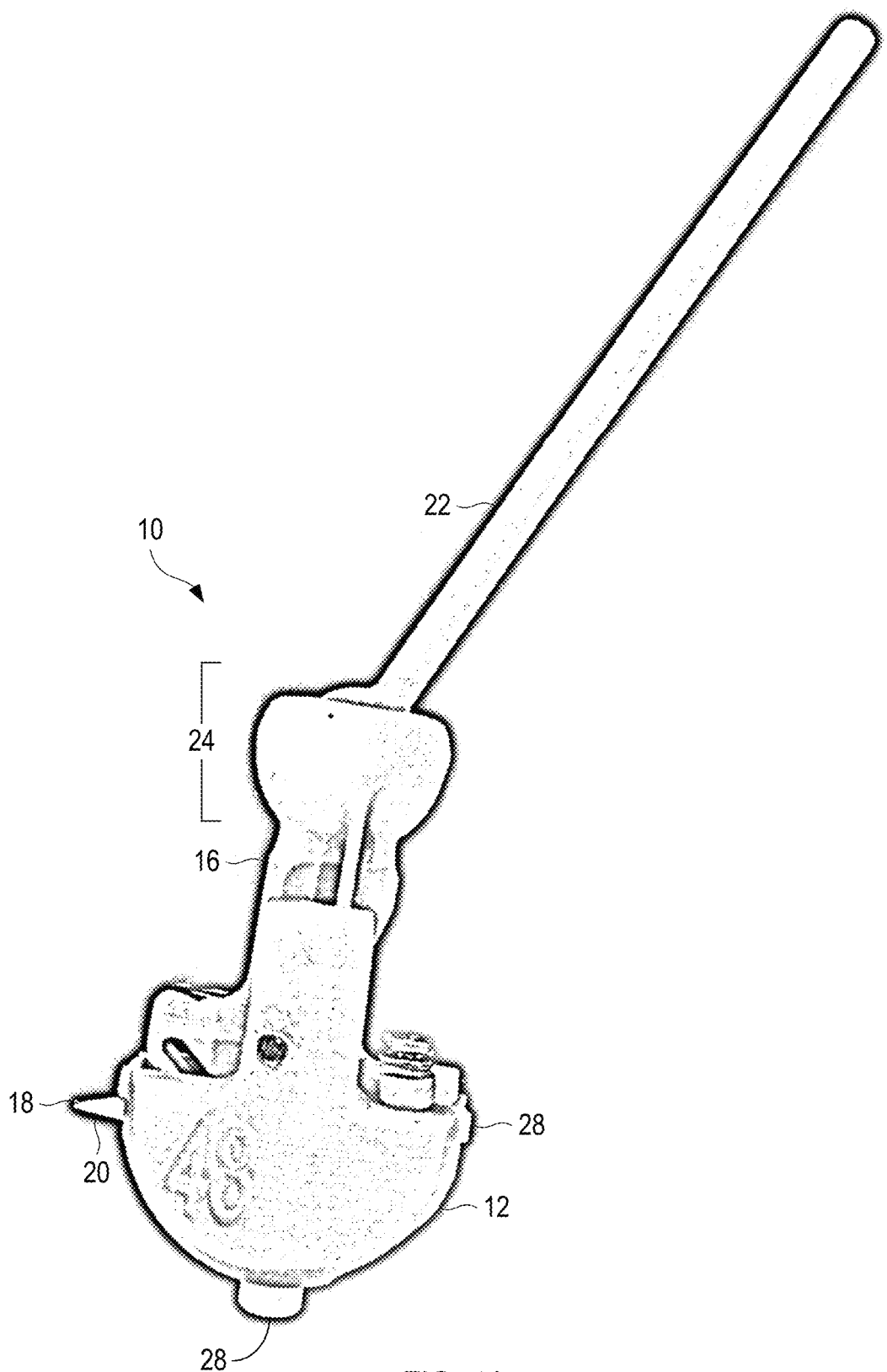
FIG. 10 shows a side view of the system of FIG. 1, in which the translator is positioned between the first and second translator positions, in accordance with some examples.

FIG. 10 shows a side view of the system 10, in which the translator 16 is positioned between the first and second translator positions, in accordance with some examples.

Figure 11:
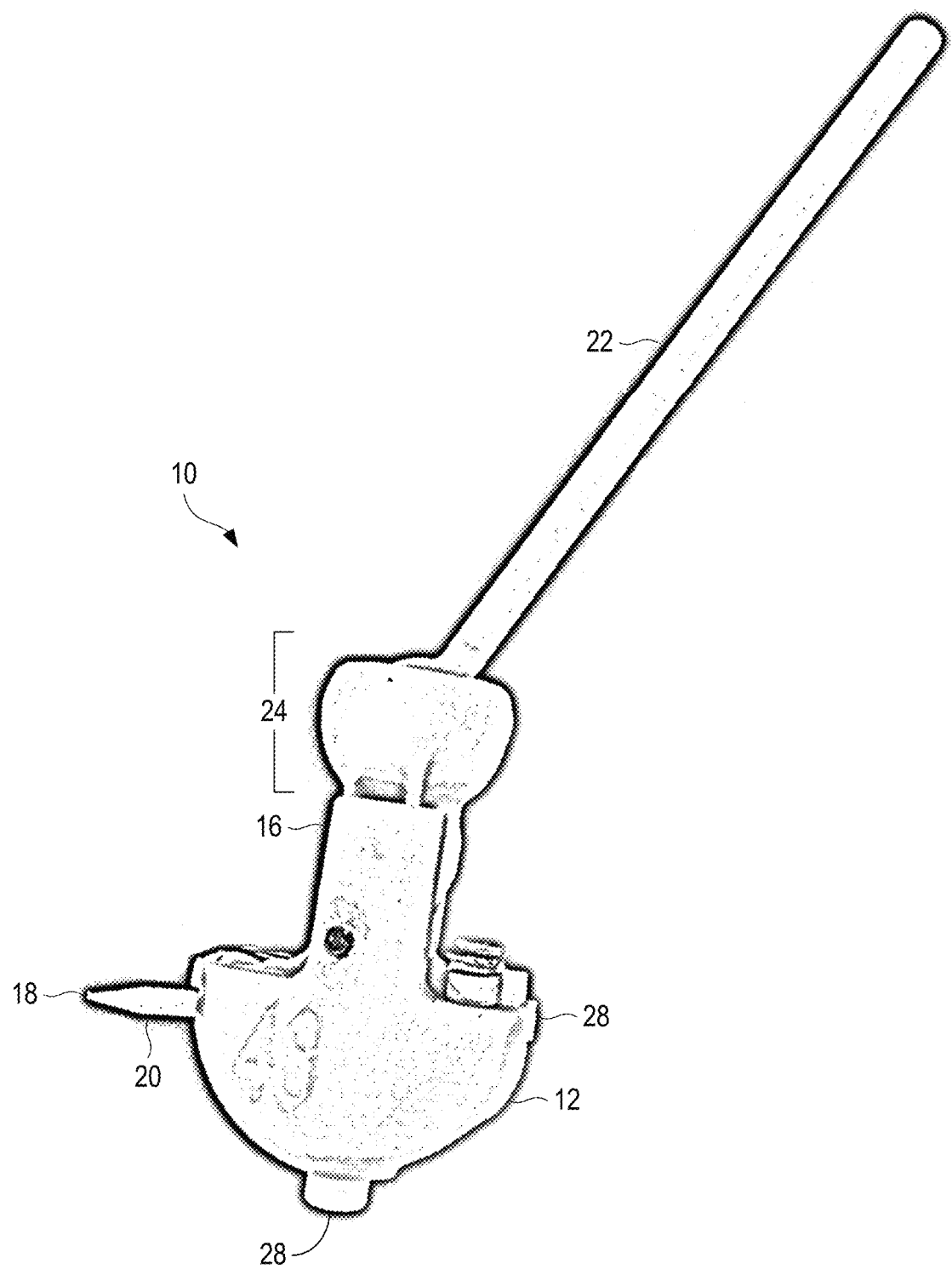
FIG. 11 shows a side view of the system of FIG. 1, in which the translator is positioned at the second translator position, in accordance with some examples.

FIG. 11 shows a side view of the system 10, in which the translator 16 is positioned at the second translator position, in accordance with some examples.

The system 10, such as a punch, can form a pilot hole to secure a securable element 14, such as a cup. The cup can be an acetabular cup. The cup can have a base curvature that is spherical and is centered on the translator axis (T). The securable element 14 can include an aperture 26, which can optionally be one of a plurality of apertures 26 that each extend through the securable element 14.

A saddle 12 can removably attach to the securable element 14, such as the acetabular cup. The saddle 12 can have an exterior surface that is concave and configured to contact a convex interior of the securable element 14 during use. The exterior surface of the saddle 12 can have a base curvature (e.g., a radius of curvature) that equals or substantially equals a base curvature of a concave interior surface of the securable element 14. Other suitable shapes and configurations can also be used.

Because the saddle 12 can be shaped with an exterior curvature that can match an interior curvature of the securable element 14, the saddle 12 and the securable element 14 can additionally include complementary aperture-selection features 28 that can help ensure that the saddle 12 is positioned in one of a finite number of specified positions with respect to the securable element 14. The saddle 12 can include aperture-selection features 28 that can mate with complementary aperture-selection features 28 on the securable element 14 when the saddle 12 is removably attached to the securable element 14.

The aperture-selection features 28 can help ensure that a specified location on the saddle 12, such as a bottom of the partial sphere of the saddle 12, becomes aligned with a corresponding location on the securable element 14, such as a bottom of the partial sphere of the securable element 14, when the saddle 12 is removably attached to the securable element 14. The aperture-selection features 28 of the saddle 12 can be configured such that the translator axis (T) can remain in a same location for selection of any of the plurality of apertures 26 of the securable element 14. For example, for a naming convention in which the securable element 14 has an open end facing upward, the saddle 12 can include an axial protrusion that is centered on a bottom of the saddle 12, which can engage a corresponding axial aperture at a bottom of the securable element 14 when the saddle 12 is removably attached to the securable element 14. Alternatively, the saddle 12 can include an axial aperture that is centered on a bottom of the saddle 12, which can engage a corresponding axial protrusion at a bottom of the securable element 14 when the saddle 12 is removably attached to the securable element 14. Other elements can also be used to properly align the bottoms (or other suitable locations) of the saddle 12 and the securable element 14. Other naming conventions can also be used; the terms bottom and top are used herein only for convenience, and are not intended to be limiting in any manner.

The aperture-selection features 28 can also allow selection of one of the plurality of apertures 26. For example, the saddle 12 can include indentations that are spaced around a circumference of the saddle 12, and the securable element 14 can include corresponding protrusions that are spaced around a circumference of the securable element 14. Alternatively, the saddle 12 can include protrusions that are spaced around a circumference of the saddle 12, and the securable element 14 can include indentations that are spaced around a circumference of the securable element 14. The protrusions can engage with the indentations when the saddle 12 is positioned at a suitable azimuthal position, such as when the punch element 20 (described below) aligns with one of the apertures 26 of the securable element 14.

A translator 16 can be confined by the saddle 12. The saddle 12 can allow the translator 16 to move along a translator axis (T) between a first translator position and a second translator position. The translator axis (T) can extend from a center (or a bottom) of the saddle 12, in a direction oriented orthogonal or substantially orthogonal to a top of the saddle 12 or a to a top of the securable element 14. The plurality of apertures 26 through the securable element 14 can be distributed circumferentially around the translator axis (T) when the saddle 12 is removably attached to the securable element 14. The saddle 12 can include a first groove 30 and a second groove (not shown) disposed on opposite sides of the translator axis (T) and each oriented parallel or substantially parallel to the translator axis (T). The translator 16 can include a first protrusion 32 that can slidably engage the first groove and a second protrusion (not shown) that can slidably engage the second groove.

A punch element 20 can be movably coupled to the saddle 12 and the translator 16. When the saddle 12 is removably attached to the securable element 14, moving the translator 16 from the first translator position toward the second translator position can advance a tip 18 of the punch element 20 from the saddle 12 through the securable element 14 along a punch axis (P) that is angled with respect to the translator axis (T). The saddle 12 can further confine the punch element 20 to move along the punch axis (P). Advancing the translator 16 toward the securable element 14 to move the translator 16 from the first translator position toward the second translator position can advance the tip 18 of the punch element 20 from the saddle 12 through an aperture 26 in the acetabular cup into the bone along the punch axis (P).

Because the aperture-selection features 28 can allow selection of one of the plurality of apertures 26, the aperture-selection features 28 can help ensure that the punch axis (P) can extend through the aperture 26 in the securable element 14 when the saddle 12 is removably attached to the securable element 14.

The punch axis (P) can optionally be orthogonal or substantially orthogonal to the translator axis (T). The translator axis (T) and the punch axis (P) can intersect and can define a plane (PL). The translator 16 can include a first slot 34 and a second slot 36. The first slot 34 and the second slot 36 can be parallel or substantially parallel to each other and disposed on opposite sides of the plane (PL). The first slot 34 and the second slot 36 can be angled with respect to the translator axis (T). The first slot 34 and the second slot 36 can be angled with respect to the punch axis (P). The punch element 20 can include a first protrusion 38 that extends into the first slot 34 and a second protrusion 40 that extends into the second slot 36. The angling of the first and second slots 34, 36, with respect to the translator axis (T) and the punch axis (P), can determine how quickly the punch element 20 moves when the translator 16 is advanced. For example, the first and second slots 34, 36 can be angled at 45 degrees or at about 45 degrees with respect to both the translator axis (T) and the punch axis (P). For such angling, the punch element 20 can move in substantially a 1:1 relationship with the translator 16, so that moving the translator 16 by 1 mm can move the punch element 20 by 1 mm or about 1 mm. Other numerical examples can also be used. Other anglings are also possible. For example, the first and second slots 34, 36 can be angled to be more closely aligned with the translator axis (T) than the punch axis (P). For such angling, a relatively large movement of the translator 16 can produce a relatively small movement of the punch element 20. As another example, the first and second slots 34, 36 can be angled to be more closely aligned with the punch axis (P) than the translator axis (T). For such angling, a relatively small movement of the translator 16 can produce a relatively large movement of the punch element 20.

The saddle 12 can be positioned with respect to the securable element 14 when the translator 16 is at the first translator position. The tip 18 of the punch element 20 may not extend away from the saddle 12 when the translator 16 is at the first translator position. Such positioning of the punch element 20 can help ensure that the punch element 20 does not contact the interior of the securable element 14 or interfere with any apertures 26 of the securable element 14 while the saddle 12 is being positioned.

The tip 18 of the punch element 20 can extend away from the saddle 12 when the translator 16 is at the second translator position. The punch element 20 can extend through the securable element 14, optionally to a specified depth, when the saddle 12 is removably attached to the securable element 14 and the translator 16 is at the second translator position. The tip 18 of the punch element 20 can advance to a specified distance beyond an outer surface of the securable element 14 when the translator 16 is at the second translator position and when the saddle 12 is removably attached to the securable element 14.

An impaction stem 22 can be coupled to the translator 16 by a joint 24, such as a ball-and-socket joint. The impaction stem 22 can impart motion to the translator 16. An end of the impaction stem 22 can be coupled to an end of the translator 16. During use, a practitioner can grip the impaction stem 22, and force the impaction stem 22 toward and away from the saddle 12. The movement of the impaction stem 22 can move the translator 16 along the translator axis (T) between the first and second translator positions. The movement of the translator 16 along the translator axis (T) in turn can move the punch element 20 along the punch axis (P). This movement can extend the punch element 20 through a selected aperture 26 in the securable element 14 and can withdraw the punch element 20 from the selected aperture 26. In some examples, through repeated movement of the impaction stem 22, the practitioner can bore a pilot hole into bone, such that after the pilot hole is bored, the practitioner can attach a bone screw through the selected aperture 26 in the securable element 14, which can secure the securable element 14 to the bone.

One technique for manufacturing the system 10 (e.g., the impaction stem 22, the translator 16, the saddle 12, and the punch element 20) is via printing on a three-dimensional (3D) printer. Three-dimensional printing can form the elements in their assembled state, including a ball-and-socket joint. The system 10 can be printed using a suitable biocompatible plastic material. For configurations in which the system 10 is 3D printed, the system 10 can be relatively inexpensive. For example, the cost of 3D printing the system 10 may be less than a cost of cleaning a sterilizing such a system 10, so that the system can be sold or distributed as a single-use (e.g., disposable) device. Other manufacturing techniques can also be used, including forming the elements separately and assembling them.

Figure 12:
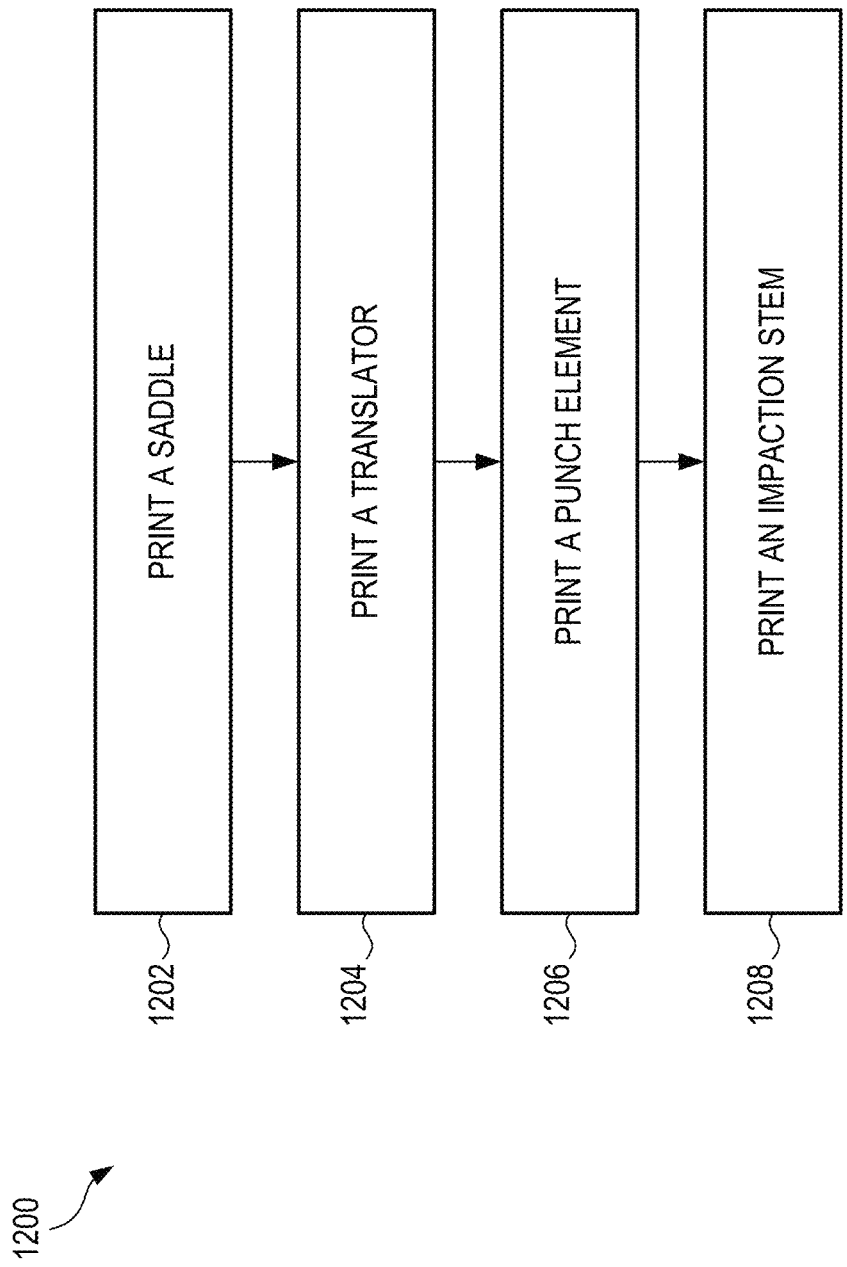
FIG. 12 shows a flowchart of an example of a method for producing a system for forming a pilot hole to secure a securable element, in accordance with some examples.

FIG. 12 shows a flowchart of an example of a method 1200 for producing a system for forming a pilot hole to secure a securable element, such as 14, in accordance with some examples. The method 1200 can be used to produce the system 10 shown in FIGS. 1-11, or produce other systems. The method 1200 of FIG. 12 is but one example of a method for producing a system for forming a pilot hole to secure a securable element; other methods can also be used.

At operation 1202, the method 1200 can include, with a three-dimensional printer, printing a saddle, such as 12, that is configured to removably attach to the securable element, such as 14.

At operation 1204, the method 1200 can include, with the three-dimensional printer, printing a translator, such as 16, that is confined by the saddle, such as 12. The saddle can allow the translator to move along a translator axis between a first translator position and a second translator position.

At operation 1206, the method 1200 can include, with the three-dimensional printer, printing a punch element, such as 20, that is movably coupled to the saddle and the translator such that when the saddle is removably attached to the securable element, moving the translator from the first translator position toward the second translator position advances a tip, such as 18, of the punch element from the saddle through the securable element along a punch axis that is angled with respect to the translator axis.

At operation 1208, the method 1200 can include, with the three-dimensional printer, printing an impaction stem, such as 22, that is coupled to the translator by a joint, such as 24, and configured to impart motion to the translator. An end of the impaction stem can be coupled to an end of the translator by a ball-and-socket joint.

EXAMPLES

To further illustrate the device, related system, and/or and related method discussed herein, a non-limiting list of examples is provided below. Each of the following non-limiting examples can stand on its own or can be combined in any permutation or combination with any one or more of the other examples.

In Example 1, a system for forming a pilot hole to secure a securable element can include: a saddle configured to removably attach to the securable element; a translator confined by the saddle, the saddle allowing the translator to move along a translator axis between a first translator position and a second translator position; a punch element movably coupled to the saddle and the translator such that when the saddle is removably attached to the securable element, moving the translator from the first translator position toward the second translator position advances a tip of the punch element from the saddle through the securable element along a punch axis that is angled with respect to the translator axis; and an impaction stem coupled to the translator by a joint and configured to impart motion to the translator.

In Example 2, the system of Example 1 can optionally be configured such that the tip of the punch element does not extend away from the saddle when the translator is at the first translator position; the tip of the punch element extends away from the saddle when the translator is at the second translator position; and the punch element extends through the securable element when the saddle is removably attached to the securable element and the translator is at the second translator position.

In Example 3, the system of any one of Examples 1-2 can optionally be configured such that the securable element comprises a cup having a base curvature that is spherical and is centered on the translator axis.

In Example 4, the system of any one of Examples 1-3 can optionally be configured such that the punch axis is orthogonal to the translator axis.

In Example 5, the system of any one of Examples 1-4 can optionally be configured such that the tip of the punch element advances to a specified distance beyond an outer surface of the securable element when the translator is at the second translator position and when the saddle is removably attached to the securable element.

In Example 6, the system of any one of Examples 1-5 can optionally be configured such that: the securable element includes an aperture; and the punch axis extends through the aperture when the saddle is removably attached to the securable element.

In Example 7, the system of any one of Examples 1-6 can optionally be configured such that: the aperture is one of a plurality of apertures that each extend through the securable element; the saddle includes aperture-selection features that mate with complementary aperture-selection features on the securable element when the saddle is removably attached to the securable element; and the aperture-selection features allow selection of one of the plurality of apertures.

In Example 8, the system of any one of Examples 1-7 can optionally be configured such that: the plurality of apertures is distributed circumferentially around the translator axis when the saddle is removably attached to the securable element; and the aperture-selection features are configured such that the translator axis remains in a same location for selection of any of the plurality of apertures.

In Example 9, the system of any one of Examples 1-8 can optionally be configured such that the saddle includes an axial protrusion that is centered on the translator axis and is configured to engage a corresponding axial aperture on the securable element when the saddle is removably attached to the securable element.

In Example 10, the system of any one of Examples 1-9 can optionally be configured such that: the saddle includes a first groove and a second groove disposed on opposite sides of the translator axis and each oriented parallel to the translator axis; and the translator includes a first protrusion that slidably engages the first groove and a second protrusion that slidably engages the second groove.

In Example 11, the system of any one of Examples 1-10 can optionally be configured such that the impaction stem is coupled to the translator by a ball-and-socket joint.

In Example 12, the system of any one of Examples 1-11 can optionally be configured such that an end of the impaction stem is coupled to an end of the translator.

In Example 13, the system of any one of Examples 1-12 can optionally further include the securable element.

In Example 14, in a method for producing a system for forming a pilot hole to secure a securable element, the method can include, with a three-dimensional printer: printing a saddle configured to removably attach to the securable element; printing a translator confined by the saddle, the saddle allowing the translator to move along a translator axis between a first translator position and a second translator position; printing a punch element movably coupled to the saddle and the translator such that when the saddle is removably attached to the securable element, moving the translator from the first translator position toward the second translator position advances a tip of the punch element from the saddle through the securable element along a punch axis that is angled with respect to the translator axis; and printing an impaction stem coupled to the translator by a joint and configured to impart motion to the translator.

In Example 15, the method of Example 14 can optionally be configured such that an end of the impaction stem is coupled to an end of the translator by a ball-and-socket joint.

In Example 16, a system for forming a pilot hole can include: an acetabular cup; a saddle configured to removably attach to the acetabular cup; a translator confined by the saddle, the saddle allowing the translator to move along a translator axis between a first translator position and a second translator position; a punch element movably coupled to the saddle and the translator such that when the saddle is removably attached to the acetabular cup, advancing the translator toward the acetabular cup to move the translator from the first translator position toward the second translator position advances a tip of the punch element from the saddle through an aperture in the acetabular cup into the bone along a punch axis that is angled with respect to the translator axis; and an impaction stem coupled to an end of the translator by a ball-and-socket joint and configured to impart motion to the translator.

In Example 17, the system of Example 16 can optionally be configured such that: the tip of the punch element does not extend away from the saddle when the translator is at the first translator position; the tip of the punch element extends away from the saddle when the translator is at the second translator position; and the punch element extends through the aperture in the acetabular cup to a specified depth into the bone when the saddle is removably attached to the aperture in the acetabular cup and the translator is at the second translator position.

In Example 18, the system of any one of Examples 16-17 can optionally be configured such that: the aperture is one of a plurality of apertures that each extend through the acetabular cup; the saddle includes aperture-selection features that mate with complementary aperture-selection features on the acetabular cup when the saddle is removably attached to the acetabular cup; and the aperture-selection features allow selection of one of the plurality of apertures.

In Example 19, the system of any one of Examples 16-18 can optionally be configured such that: the plurality of apertures is distributed circumferentially around the translator axis when the saddle is removably attached to the acetabular cup; and the aperture-selection features are configured such that the translator axis remains in a same location for selection of any of the plurality of apertures.

In Example 20, the system of any one of Examples 16-19 can optionally be configured such that: the saddle includes a first groove and a second groove disposed on opposite sides of the translator axis and each oriented parallel to the translator axis; the translator includes a first protrusion that slidably engages the first groove and a second protrusion that slidably engages the second groove; the translator axis and the punch axis intersect and define a plane; the translator includes a first slot and a second slot; the first slot and the second slot are parallel to each other and disposed on opposite sides of the plane; the first slot and the second slot are angled with respect to the translator axis; the first slot and the second slot are angled with respect to the punch axis; the punch element includes a first protrusion that extends into the first slot and a second protrusion that extends into the second slot; and the saddle is further configured to confine the punch element to move along the punch axis.

What is claimed is:

1. A system for forming a pilot hole in a bone to secure a securable element to the bone, the system comprising:
   the securable element;
   a saddle configured to removably attach to the securable element;
   a translator confined and directly contacted by the saddle, the saddle allowing the translator to move along a translator axis between a first translator position and a second translator position;
   a punch element movably coupled to the saddle and the translator such that when the saddle is removably attached to the securable element, moving the translator from the first translator position toward the second translator position is configured to advance a tip of the punch element from the saddle through one of a plurality of apertures in the securable element to form the pilot hole in the bone along a punch axis that is angled with respect to the translator axis; and
   an impaction stem coupled to the translator by a joint and configured to impart motion to the translator,
   wherein the saddle includes aperture-selection features that mate with complementary aperture-selection features on the securable element when the saddle is removably attached to the securable element to allow selection of the one of the plurality of apertures in the securable element.

2. The system of claim 1, wherein:
   the tip of the punch element does not extend away from the saddle when the translator is at the first translator position;
   the tip of the punch element extends away from the saddle when the translator is at the second translator position; and
   the punch element extends through the securable element when the saddle is removably attached to the securable element and the translator is at the second translator position.

3. The system of claim 1, wherein the securable element comprises a cup having a base curvature that is spherical and is centered on the translator axis.

4. The system of claim 1, wherein the punch axis is orthogonal to the translator axis.

5. The system of claim 1, wherein the tip of the punch element advances to a specified distance beyond an outer surface of the securable element when the translator is at the second translator position and when the saddle is removably attached to the securable element.

6. The system of claim 1, wherein:
   the plurality of apertures is distributed circumferentially around the translator axis when the saddle is removably attached to the securable element; and
   the aperture-selection features of the saddle and the complementary aperture-selection features on the securable element are configured such that the translator axis remains in a same location for selection of any of the plurality of apertures.

7. The system of claim 1, wherein the saddle includes an axial protrusion that is centered on the translator axis and is configured to engage a corresponding axial aperture on the securable element when the saddle is removably attached to the securable element.

8. The system of claim 1, wherein:
the saddle includes a first groove and a second groove disposed on opposite sides of the translator axis and each oriented parallel to the translator axis; and
the translator includes a first protrusion that slidably engages the first groove and a second protrusion that slidably engages the second groove.

9. The system of claim 1, wherein the joint is a ball-and-socket joint.

10. The system of claim 1, wherein an end of the impaction stem is coupled to an end of the translator.

11. A method for producing a system for forming a pilot hole in a bone to secure a securable element to the bone, the method comprising, with a three-dimensional printer:
printing the securable element;
printing a saddle configured to removably attach to the securable element;
printing a translator confined and directly contacted by the saddle, the saddle allowing the translator to move along a translator axis between a first translator position and a second translator position;
printing a punch element movably coupled to the saddle and the translator such that when the saddle is removably attached to the securable element, moving the translator from the first translator position toward the second translator position is configured to advance a tip of the punch element from the saddle through one of a plurality of apertures in the securable element to form the pilot hole in the bone along a punch axis that is angled with respect to the translator axis; and
printing an impaction stem coupled to the translator by a joint and configured to impart motion to the translator,
wherein the saddle includes aperture-selection features that mate with complementary aperture-selection features on the securable element when the saddle is removably attached to the securable element to allow selection of the one of the plurality of apertures in the securable element.

12. The method of claim 11, wherein the joint is a ball-and-socket joint.

13. A system for forming a pilot hole in a bone, the system comprising:
an acetabular cup configured to be secured to the bone;
a saddle configured to removably attach to the acetabular cup;
a translator confined and directly contacted by the saddle, the saddle allowing the translator to move along a translator axis between a first translator position and a second translator position;
a punch element movably coupled to the saddle and the translator such that when the saddle is removably attached to the acetabular cup, advancing the translator toward the acetabular cup to move the translator from the first translator position toward the second translator position is configured to advance a tip of the punch element from the saddle through one of a plurality of apertures in the acetabular cup into the bone to form the pilot hole in the bone along a punch axis that is angled with respect to the translator axis; and
an impaction stem coupled to an end of the translator by a ball-and-socket joint and configured to impart motion to the translator,
wherein the saddle includes aperture-selection features that mate with complementary aperture-selection features on the acetabular cup when the saddle is removably attached to the acetabular cup to allow selection of the one of the plurality of apertures in the acetabular cup.

14. The system of claim 13, wherein:
the tip of the punch element does not extend away from the saddle when the translator is at the first translator position;
the tip of the punch element extends away from the saddle when the translator is at the second translator position; and
the punch element is configured to extend through the one of the plurality of apertures in the acetabular cup to a specified depth into the bone when the saddle is removably attached to the acetabular cup and the translator is at the second translator position.

15. The system of claim 13, wherein:
the plurality of apertures is distributed circumferentially around the translator axis when the saddle is removably attached to the acetabular cup; and
the aperture-selection features of the saddle and the complementary aperture-selection features on the acetabular cup are configured such that the translator axis remains in a same location for selection of any of the plurality of apertures.

16. The system of claim 13, wherein:
the saddle includes a first groove and a second groove disposed on opposite sides of the translator axis and each oriented parallel to the translator axis;
the translator includes a first protrusion that slidably engages the first groove and a second protrusion that slidably engages the second groove;
the translator axis and the punch axis intersect and define a plane;
the translator includes a first slot and a second slot;
the first slot and the second slot are parallel to each other and disposed on opposite sides of the plane;
the first slot and the second slot are angled with respect to the translator axis;
the first slot and the second slot are angled with respect to the punch axis;
the punch element includes a first protrusion that extends into the first slot and a second protrusion that extends into the second slot; and
the saddle is further configured to confine the punch element to move along the punch axis.

* * * * *